United States Patent [19]

Lyons

[11] 3,957,827
[45] May 18, 1976

[54] HYDROGENATION OF CARBOXYLIC ACID ANHYDRIDES TO LACTONES OR ESTERS BY HOMOGENEOUS CATALYSIS

[75] Inventor: James E. Lyons, Wallingford, Pa.

[73] Assignee: Sun Ventures, Inc., St. Davids, Pa.

[22] Filed: Oct. 17, 1974

[21] Appl. No.: 515,771

[52] U.S. Cl. .................. 260/343.3 R; 252/431 N;
252/431 P; 260/343.6; 260/468 R; 260/469;
260/476 R; 260/488 R
[51] Int. Cl.² ............... C07C 68/00; C07D 307/20;
C07D 307/88
[58] Field of Search ......... 260/343.3, 343.6, 488 R,
260/469, 476 R, 468 R

[56] References Cited
UNITED STATES PATENTS

| | | | |
|---|---|---|---|
| 2,072,861 | 3/1937 | Amend et al. | 260/343.6 |
| 2,772,292 | 11/1956 | McShane et al. | 260/343.6 |
| 2,867,628 | 1/1959 | Cass | 260/343.6 |
| 3,110,747 | 11/1963 | Mullineaux | 260/683.9 |
| 3,312,718 | 4/1967 | Woskow | 260/343.6 |
| 3,492,314 | 1/1970 | Asano et al. | 260/343.6 |

*Primary Examiner*—James A. Patten
*Attorney, Agent, or Firm*—J. Edward Hess; Donald R. Johnson; Stanford M. Back

[57] ABSTRACT

γ-Lactones may be selectively prepared by the hydrogenation of cyclic carboxylic acid anhydrides under mild conditions in a homogeneous solution in the presence of a ruthenium catalyst of the formula

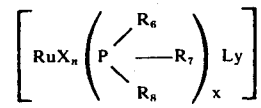

wherein X is hydrogen, chlorine, bromine, iodine, or lower alkyl; $n$ is an integer of from 0–2, but when $n$ is 2, X may be the same or different; L is a neutral ligand, olefin, or CO; $y$ is an integer of from 0–3, but when $y$ is 2 or 3, L may be the same or different; $R_6$, $R_7$ and $R_8$ are lower alkyl, cycloalkyl of from 5 to 15 carbon atoms, aryl, benzyl, or a bidentate ligand, and each of the R groups may be the same or different; and $x$ is an integer of from 1–3.

In a like manner, esters may be prepared in high yields by the selective hydrogenation of acyclic carboxylic acid anhydrides.

11 Claims, No Drawings

HYDROGENATION OF CARBOXYLIC ACID ANHYDRIDES TO LACTONES OR ESTERS BY HOMOGENEOUS CATALYSIS

BACKGROUND OF THE INVENTION

This invention relates to an improved process for the selective hydrogenation of acyclic and cyclic carboxylic acid anhydrides to esters and lactones. More particularly, this invention relates to the selective conversion of said anhydrides to esters and lactones respectively hydrogenating hydrogenating them under mild conditions in the presence of an organometallic ruthenium complex catalyst in homogeneous solution.

It is known, for example, from Kanetaka et al., Japan 71, 33,030, that succinic anhydride can be hydrogenated to $\gamma$-butyrolactone using heterogeneous catalysts which necessitate vigorous conditions: 2000°–300°C., 1500–3000 psi $H_2$. Reaction is unselective and tetrahydrofuran is usually formed as a by-product.

SUMMARY OF THE INVENTION

In accordance with the present invention, it has now been found that acyclic and cyclic carboxylic acid anhydrides can be hydrogenated to form the corresponding esters and lactones respectively by by carrying out the reaction in the presence of a homogeneous ruthenium catalyst of the formula

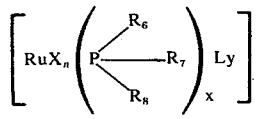

wherein X is hydrogen, chlorine, bromine, iodine, or lower alkyl; $n$ is an integer of from 0–2, but when $n$ is 2, X may be the same or different; L is a neutral ligand, olefin, or CO; $y$ is an integer of from 0–3, but when $y$ is 2 or 3, L may be the same or different; $R_6$, $R_7$ and $R_8$ are lower alkyl, cycloalkyl of from 5 to 15 carbon atoms, aryl, benzyl, or a bidentate ligand, and each of the R groups may be the same or different; and $x$ is an integer of from 1–3, at temperatures in the range of from about 50° 150°C., preferably 90° to 110°C., and at about 40 to 400 psi $H_2$, preferably 100 to 150 psi. The reaction is characterized by being selective, often quantitative in yield, and most desirably does not proceed beyond the lactone or ester.

These reactions may best be described by the following reaction schemes:

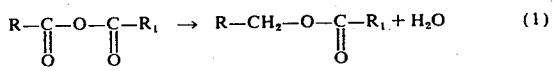

wherein R and $R_1$ are lower alkyl, cycloalkyl of from 5 to 15 carbon atoms, or aryl; wherein the R groups may be the same or different; and

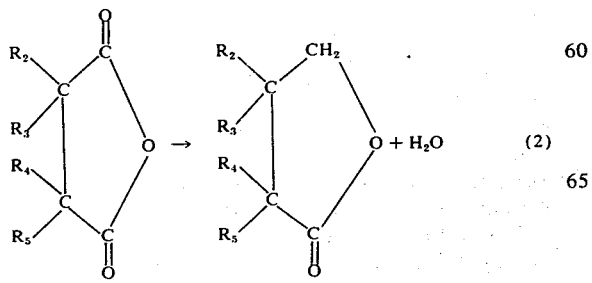

wherein each of $R_2$, $R_3$, $R_4$ and $R_5$ is hydrogen, lower alkyl, cycloalkyl of from 5 to 15 carbon atoms, or aryl; wherein each of the R groups may be the same of different; and wherein the R groups, when taken together may form a saturated, or unsaturated, ring having from 5 to 8 carbon atoms, or an aromatic or condensed aromatic ring.

DESCRIPTION OF THE INVENTION

The starting materials comprise acyclic and cyclic carboxylic acid anhydrides, as above-defined. More particularly, the acyclic anhydrides are comprised of compounds of the formula

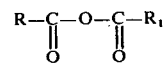

wherein R and $R_1$ are as defined above in Equation 1. Examples of acyclic anhydrides coming within the purview of this invention include acetic anhydride, propionic anhydride, benzoic acid dianhydride and mixed anhydrides of similar structure. When these compounds are hydrogenated in accordance with the process of this invention, there are obtained the corresponding esters of the formula

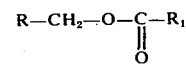

wherein R and $R_1$ are as defined above. The ester products include such compounds as ethyl acetate, butyl propionate, benzyl benzoate, and the like.

The cyclic anhydrides are comprised of compounds of the formula

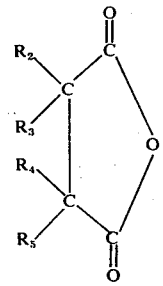

wherein each of $R_2$, $R_3$, $R_4$ and $R_5$ is as defined above in Equation 2. Examples of cyclic anhydrides falling within the scope of the invention include succinic anhydride, glutaric anhydride and the like. When these compounds are reacted in accordance with the disclosed process, there are obtained the corresponding lactones of the formula

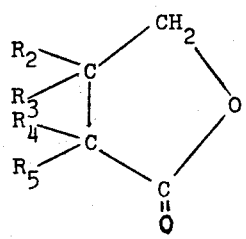

wherein each of $R_2$, $R_3$, $R_4$ and $R_5$ is as defined above, as for example γ-butyrolactone. In addition to the foregoing, the $R_{2-5}$ groups taken together may form bicyclic compounds, including those of the formula

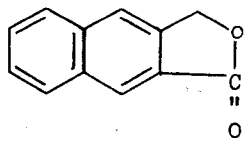

OR 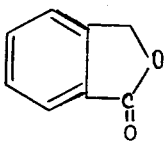

as for example phthalide from phthalic anhydride, the corresponding γ-lactone from naphthalene-1,2-dicarboxylic acid anhydride and the like.

Each of the aforedescribed products is known in the art and has established utilities. Ethyl acetate, for example, is a fast-drying solvent with applications in cellulose, shellac, vinyl resins, and the like. Likewise, γ-butyrolactone is an important industrial solvent for cellulose acetate or polystyrene as well as an intermediate for N-methyl-pyrolidone, vinyl-pyrolidone, piperidine and the like. Phthalide is useful as a co-monomer in polymer formulations, i.e. formaldehyde polymers, and in the synthethis of dyestuffs. Thus it may be said that esters and lactones generally have well-established wide industrial applications, and that the esters in particular have wide utility as solvents and plasticizers.

The ruthenium catalyst of this process, as mentioned above, has the formula

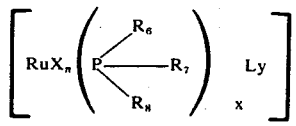

wherein X is hydrogen, chlorine, bromine, iodine, or lower alkyl; n is an integer of from 0–2, but when n is 2, X may be the same or different; L is a neutral ligand, olefin, or CO; y is an integer of from 0–3, but when y is 2 or 3, L may be the same or different; $R_6$, $R_7$ and $R_8$ are lower alkyl, cycloalkyl of from 5 to 15 carbon atoms, aryl, benzyl, or a bidentate ligand, and each of the R groups may be the same or different; and x is an integer of from 1–3. Included amongst these compounds are the catalysts $RuCl_2(PPh_3)_3$, $RuHCl(PPh_3)_3$, $RuCl_2(CO)(PPh_3)_2(C_8H_{12})$, $RuBr_2(PPh_3)_3$, $RuHBr(PPh_3)_3$, $RuCl_2(PPh_2CH_3)_3$, of which $RuCl_2(PPh_3)_3$ is preferred. See Hallman et al., J. Chem. Soc. (A), 3143, (1968), for the preparation of these compounds. Also useful are bidentate ligand catalysts such as $Ru(C_{10}H_8)$ (diphos)$_2$, and Ru(diphos)$_2$. See Chatt et al., J. Chem. Soc., 843, (1965), for their preparation.

The process may readily be carried out by contacting the acid anhydride with the ruthenium catalyst in the presence of a solvent at temperatures in the range of from about 50° to 150°C., and preferably 90° to 110°C., for a period of from 1 to 20 hours, depending upon the reactants, at a pressure of from about 40 to 400 psi $H_2$, and preferably 100 to 150 psi. The solvent is desirably an aromatic hydrocarbon such as toluene or xylene but other unreactive solvents such as chlorocarbons, fluorocarbons, ethers and the like are also suitable. The ratio of starting material to solvent is most desirably in the range of from 0.1 to 1.0, and preferably 0.3 to 0.7. The amount of catalyst employed should be about $10^{-1}$ mole to $10^{-4}$ mole per mole of starting material, and preferably $10^{-2}$ mole to $10^{-3}$ mole. The ester or lactone product is conveniently recovered by distillation, crystallization or other conventional methods.

It will be noted in both Equations 1 and 2 above that water is formed as a by-product of this hydrogenation reaction with the result that for every mole of product formed, 1 mole of water is formed which then hydrolyzes 1 mole of starting material to its corresponding acid in accordance with the following overall reaction scheme, using a cyclic anhydride as an example:

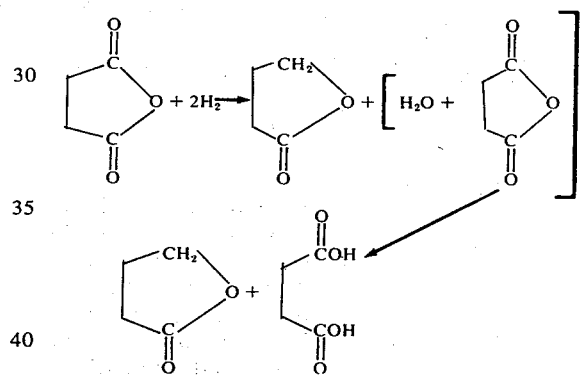

Thus it will be understood from the above that while the yield of desired lactone product is 50% by weight, it represents 100% theoretical yield. Moreover, the hydrolyzed acid may readily be recovered dehydrated, and recycled to the reactor with little, if any, resultant loss by weight of starting compound.

It will also be evident from the foregoing that if an effective water scavanger, i.e., dehydrating agent, such as a molecular sieve, $MgSO_4$, or the like is added to the reaction medium, most if not all of the attendant hydrolysis and resulting dehydration and recycle of starting anhydride may be avoided, with, of course, increased yields per pass.

The invention will now be illustrated by the following examples.

EXAMPLE 1

Succinic anhydride, 2.0 grams, toluene, 4.0 ml and [$RuCl_2(Ph_3P)_3$], 0.1 gram are stirred at 100°C under 150 psi $H_2$ for 10 hours. During the reaction the anhydride dissolves over the first 2 hours to form an orange solution which absorbs hydrogen steadily. After hydrogen adsorption has stopped, after 8 hours, the mixture is allowed to stir for an additional 2 hours under 150 psi $H_2$ and 100°C. The mixture is cooled to precipitate the acid formed during reaction and the solution contains only γ-butyrolactone and less than 1% of unidentified impurities.

EXAMPLE 2

The procedures of Example 1 are repeated, but acetic anhydride and phthalic anhydride, respectively, are substituted for the succinic anhydride starting material of this previous example. The results obtained are summarized in Table I below. The results of Example 1 are included.

TABLE I

| CATALYST | STARTING MATERIAL | PRODUCT | CONVERSION (THEORETICAL) | SELECTIVITY |
|---|---|---|---|---|
| [$RuCl_2(Ph_3*P)_3$] | Acetic Anhydride | Ethyl Acetate | 100% | 95% |
| [$RuCl_2(Ph_3P)_3$] | Phthalic Anhydride | Phthalide | 100% | 100% |
| [$RuCl_2(Ph_3P)_3$] | Succinic Anhydride | γ-Butyrolactone | 100% | 99% |

*Ph=phenyl

EXAMPLE 3

In accordance with the process of Example 2, but substituting $RuHCl(PPh_3)_3$ as the catalyst, there are obtained each of the respective products in good yield.

EXAMPLE 4

In accordance with the process of Example 1, but substituting $RuBr_2(PPh_3)_3$ as the catalyst, there is obtained γ-butyrloactone in good yield.

EXAMPLE 5

In accordance with the process of Example 1, but substituting $RuCl_2(PPh_2CH_3)_3$ as the catalyst, there is obtained γbutyrolactone in good yield.

EXAMPLE 6

Example 1 is repeated except that the catalyst is $Ru(diphos)_2$, the hydrogen pressure is 400 psi, and the temperature is 125°C. γ-butyrolactone is provided in good yield.

The invention claimed is:

1. A process for the selective hydrogenation of acyclic and cyclic carboxylic acid anhydrides to form esters or lactones comprises reacting hydrogen with (1) an acyclic compound of the formula:

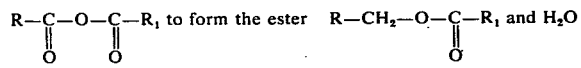

wherein R and $R_1$ are lower alkyl, cycloalkyl of from 5 to 15 carbon atoms, or aryl, wherein the R groups may be the same or different; or (2) a cyclic compound of the formula:

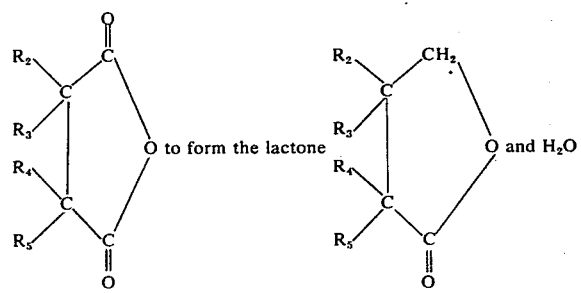

wherein $R_2$, $R_3$, $R_4$ and $R_5$ are hydrogen, lower alkyl, cycloalkyl of from 5 to 15 carbon atoms, or aryl, wherein each of the R groups may be the same or different; and wherein the R groups, taken together, may form a saturated or aromatic ring; said reaction being carried out in a homogeneous solution in the presence of a ruthenium catalyst of the formula:

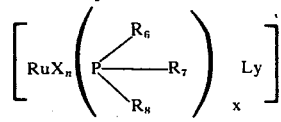

wherein X is hydrogen, chlorine, bromine, iodine, or lower alkyl; $n$ is an integer of from 0–2, but when $n$ is 2, X may be the same or different; L is a neutral ligand, olefin, or CO; $y$ is an integer of from 0–3, but when $y$ is 2 or 3, L may be the same of different; $R_6$, $R_7$ and $R_8$ are lower alkyl, cycloalkyl of from 5 to 15 carbon atoms, aryl, benzyl, or a bidentate ligand, and each of the R groups may be the same or different; and $x$ is an integer of from 1–3, at a temperature of from about 50° to 150°C., and at a hydrogen pressure of from about 40 to 400 psi.

2. The process according to claim 1 wherein the anhydride is acetic anhydride and the ester is ethyl acetate.

3. The process according to claim 1 wherein the anhydride is succinic anhydride and the lactone is γ-butyrolactone.

4. The process according to claim 1 wherein the anhydride is phthalic anhydride and the lactone is phthalide.

5. The process according to claim 1 wherein the catalyst is [$RuCl_2(Ph_3P)_3$].

6. The process according to claim 1 wherein the catalyst is $RuHCl(PPh_3)_3$.

7. The process according to claim 1 wherein the catalyst is $RuCl_2)PPh_2CH_3)_3$.

8. The process according to claim 1 wherein part of the anhydride starting material is hydrolyzed to the corresponding acid, the acid recovered and dehydrated, and the resulting anhydride recycled to the reaction.

9. The process according to claim 1 wherein the reaction is carried out in the presence of a dehydrating agent.

10. The process according to claim 9 wherein the dehydrating agent is a molecular sieve or $MgSO_4$.

11. The process according to claim 1 wherein the catalyst is present in amounts of $10^{-1}$ to $10^{-4}$ moles per mole of anhydride starting material present.

* * * * *